United States Patent [19]

Vogel et al.

[11] 4,412,855
[45] Nov. 1, 1983

[54] 2-CHLORO-N-(2'-METHOXYPROPYL)- AND 2-CHLORO-N-(2'-ETHOXYPROPYL)-2",6"-DIMETHYL-ACETANILIDE AS LONG TERM WEED KILLERS

[75] Inventors: Christian Vogel, Binningen; Rudolf Aebi, Basel, both of Switzerland

[73] Assignee: Ciba-Geigy Corporation, Ardsley, N.Y.

[21] Appl. No.: 944,816

[22] Filed: Sep. 22, 1978

Related U.S. Application Data

[63] Continuation-in-part of Ser. No. 860,016, Dec. 12, 1977, abandoned, which is a continuation-in-part of Ser. No. 688,867, May 21, 1976, abandoned, which is a continuation-in-part of Ser. No. 548,041, Feb. 7, 1975, abandoned, which is a continuation-in-part of Ser. No. 328,202, Jan. 31, 1973, abandoned.

[30] Foreign Application Priority Data

Feb. 7, 1972 [CH] Switzerland ........................ 1739/72
May 16, 1972 [CH] Switzerland ........................ 7283/72

[51] Int. Cl.$^3$ .................... A01N 37/22; C07C 103/32
[52] U.S. Cl. ........................................... 71/118; 71/76; 564/214
[58] Field of Search .................... 71/118, 562 B, 76; 564/214

[56] References Cited

U.S. PATENT DOCUMENTS

| | | | |
|---|---|---|---|
| 3,442,945 | 5/1969 | Olin | 260/562 B |
| 3,547,620 | 5/1970 | Olin | 260/562 B |
| 3,739,024 | 6/1973 | Chupp | 260/551 S |

FOREIGN PATENT DOCUMENTS

1903198 8/1970 Fed. Rep. of Germany .

Primary Examiner—Catherine L. Mills
Attorney, Agent, or Firm—Frederick H. Rabin

[57] ABSTRACT

2-Chloro-N-(2'-methoxypropyl)- and 2-chloro-N-(2'e-thoxypropyl)-2",6"-dimethyl-acetanilide are very effective agents for combating weeds and for regulating plant growth with improved stability in the soil.

4 Claims, No Drawings

2-CHLORO-N-(2'-METHOXYPROPYL)- AND 2-CHLORO-N-(2'-ETHOXYPROPYL)-2″,6″-DIMETHYL-ACETANILIDE AS LONG TERM WEED KILLERS

CROSS-REFERENCE

This application is a continuation-in-part of our application Ser. No. 860,016, filed Dec. 12, 1977, now abandoned which in turn is a continuation-in-part of our abandoned application Ser. No. 688,867, filed May 21, 1976, which in turn is a continuation-in-part of our abandoned application Ser. No. 548,041, filed Feb. 7, 1975, which in turn is a continuation-in-part of our abandoned application Ser. No. 328,202, filed Jan. 31, 1973.

This invention relates to 2-(chloro-N-2'-methoxypropyl)-and 2-chloro-N-(2'-ethoxypropyl)-2″,6″-dimethyl-acetanilide of the formula I

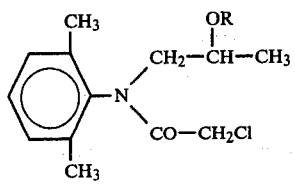

wherein R represents methyl or ethyl, to a herbicidal and plant growth regulating composition which contains at least one of the new compounds as active substance, and to a method of combating weeds and of regulating plant growth which comprises applying to the plant area a compound of formula I.

The compounds of formula I are predominantly selective pre-emergent herbicides.

Haloacetanilides having a branched alkoxypropyl side chain of the above type have not hitherto been described in the literature. The excellently herbicidal activities and plant growth regulating properties of the compounds of formula I are the more surprising as alkoxypropyl substituted haloacetanilides are said to have a disappointingly inferior herbicidal activity contrasted with haloacetanilides having an alkoxymethyl side chain (Example 85 of U.S. Pat. No. 3,547,620). Moreover, compounds of the above formula I of this invention exhibit a significantly improved stability in the soil.

For practical purposes, it is desirable that a selective herbicide used to protect a plant culture
should be tolerated by the cultivated plant over a broad range of application rates (in order to avoid plant damage by inadvertent overdosage)
should possess an appropriate weedicidal spectrum, and a duration of activity such that one application per crop season will suffice to keep the treated locus weedfree through to harvest.
The last mentioned desideratum is of particular importance.

A broad-spectrum selective herbicide is of no real practical utility if it breaks down within 2 or 3 weeks of application thus requiring several applications per season with the concommitent increase in labour and costs.

A pre-emergent herbicide with sufficient in-soil durability avoids the necessity of further herbicides post-emergent application.

The ideal selective herbicide possesses an activity spectrum proper to the crop to be protected, a high weedicidal activity and a suitably long life after application. These criteria and desiderata apply equally to plant-growth regulating substances. All have to be taken into account when selecting a suitable herbicidal or plant-growth regulating agent.

The compounds of the above formula I display an ideal combination of the desired activity on weeds, tolerance on crops and long lasting effectiveness when used before emergence of the plants.

When used for post-emergent treatment the compounds of the formula I act as plant-growth regulators in that they will delay or inhibit the growth of many mono- or di-cotyledonous plants be they plant cultures or weeds. Thus the growth rate of grassland (comprising for example Poa pratensis, Agrostis tenuis, Festuca rubra) treated with 5 kg/hectare of active substance shortly after the first cutting in spring is reduced by half an observation period of 60 days being used as a basis. The primary consequence of this activity is a reduction of the plant size in particular of its height. Accompanying changes in plant morphology may be observed. As a direct result of the reduction in height the plant gains in sturdiness, the leaves and stems grow stronger and in the case of monocotyledones the reduction of the internodal distance results in greater resistance to bending and breaking. A further benefit of reduced growth in plant cultures and for example lawns, sports fields and other grassed-over areas is the saving in manure and/or fertilizer and in the case of the latter the reduced frequency at which they must be mown or scythed. A typical area of application would be to roadsides where the easy maintenance of medium growth-height throughout the vegetation period is desirable.

The active substances of the formula I may of course be used in conjunction with other active substances.

The new chloroacetanilides of the formula I are manufactured by reacting a N-substituted aniline of the formula II

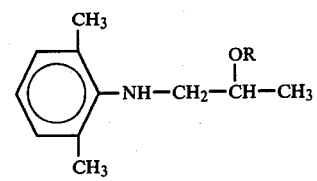

with a chloroacetylating agent, preferably an anhydride or halide of chloroacetic acid. In formula II, R represents methyl or ethyl.

It is also possible to manufacture the compounds of the formula I in such a manner that 2,6-xylidine is reacted with 1-halopropan-2-ol, in which "halo" represents chlorine or bromine, then the resulting compound of the formula IIa

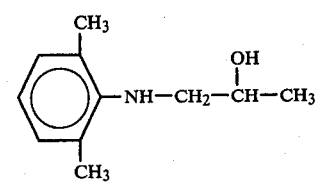

is reacted with a chloroacetylating agent, preferably an anhydride or halide of chloroacetic acid, and finally, the still free OH group is etherified in the conventional way with methanol or ethanol respectively in acid medium (e.g. H₂SO₄) and under mild conditions.

The reactions can be carried out in the presence or absence of solvents or diluents which are inert towards the reactants. Examples of suitable solvents or diluents are: aliphatic, aromatic or halogenated hydrocarbons, such as benzene, toluene, xylene, petroleum ether, chlorobenzene, methylene chloride, ethylene chloride, chloroform; ethers and ethereal compounds, such as dialkyl ethers, dioxane, tetrahydrofuran; nitriles, such as acetonitrile; N,N-dialkylated amides, such as dimethyl formamide; also dimethyl sulphoxide, and also mixtures of these solvents.

As suitable chloroacetylating agents there are preferably used chloroacetic anhydride and chloroacetyl chloride. However, it is also possible to carry out the reaction with chloroacetic acid or its esters. The reaction temperatures are between 0° and 200° C., preferably between 20° and 100° C. Often, especially if chloroacetyl halides are used, the chloroacetylation is carried out in the presence of an acid binding agent. Suitable acid binding agents are: tertiary amines, such as trialkylamines, e.g. triethylamine, pyridine and pyridine bases, or inorganic bases, such as the oxides and hydroxides, hydrogen carbonates and carbonates of alkali and alkaline earth metals. Furthermore, it is also possible to use the corresponding aniline of the formula II as acid binding agent, in which case it must be used in excess.

The starting materials can be easily manufactured by methods which are known per se, for example:

(a) by condensation of 2,6-xylidine with an alkoxyalkanal OHC—CH(CH₃)—OR (with R=methyl or ethyl) to give the corresponding azomethine of the formula III

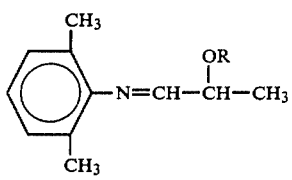

and subsequent catalytic hydrogenation to the N-alkoxypropyl-2,6-dimethylaniline of the formula II;

(b) by reaction of 2,6-xylidine with a compound of the formula IV

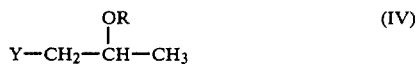

wherein R=methyl or ethyl and Y represents a halogen atom or another acid radical, in particular an alkylsulphonic acid radical or an arylsulphonic acid radical. Compounds similar to formula IV with benzenesulphonic acid radicals Y are described e.g. in Can. J. Chem. 33, 1207, and those with tosyloxy radicals in British Pat. No. 869,083;

The following Example ilustrates the invention, including the manufacture of a starting material.

EXAMPLE 1

(a) Manufacture of the Starting Material:

A solution consisting of 121 g (1.0 mole), of 2,6-xylidine, 70 g (0.5 mole) 1-bromo-2-propanol and 100 ml of absolute toluene is heated under reflux for 24 hours. After cooling 300 ml 2 N sodium hydroxide are added. The organic layer is separated, washed with water until neutral, dried over sodium sulfate and evaporated in vacuo. The crude product is fractionally distilled to yield 59.6 g of N-(2'-hydroxypropyl)-2,6-xylidine, b.p. 81°-83°/0.1 Torr.

(b) 37.7 g (0.21 mole) of the product obtained according to (a) are dissolved in 100 ml of benzene. After addition of 23.3 g (0.22 mole) of sodium carbonate 24.9 g (0.22 mole) of chloroacetyl chloride are added dropwise the temperature being kept below 30° C. Stirring is continued overnight and the mixture is then diluted with 100 ml of diethyl ether and washed with a total of 200 ml of water i.e. until neutral. The organic layer is separated, dried with magnesium sulfate and evaporated. The residue is crystallised from 200 ml of isopropyl ether. 43.5 g of 2-chloro-N-(2'-hydroxypropyl)-2'',6''-dimethyl-acetanilide are obtained, m.p. 83°-85° C.

(c) 10.2 (0.04 mole) of the intermediate product obtained are dissolved in 40 ml of absolute methanol and after addition of 2 ml of conc. sulfuric acid the solution is heated under reflux for 25 hours. The mixture is then evaporated under reduced pressure. The residue is dissolved in 200 ml of diethyl ether and the solution obtained washed twice with water, dried over magnesium sulfate and again evaporated. After distillation of the oily residue 6.5 g of 2-chloro-N-(2'-methoxypropyl)-2'',6''-dimethyl-acetanilide are obtained, b.p. 120°-122° C./0,001 Torr, $n_D^{20}$ 1.5325 (Compound No. 1). 2-chloro-N-(2'-ethoxypropyl)-2'',6''-dimethyl-acetanilide may be prepared accordingly, $n_D^{20}$ 1.5126 (Comp. No. 2).

Another starting material obtained by condensation of 2,6-xylidine with 2-methoxypropionaldehyde OHC—CH(CH₃)—OCH₃ and subsequent hydrogenation of the intermediate is N-(2'-methoxypropyl)-2,6-xylidine, b.p. 54°-57° C./0.04 Torr.

The active substances according to the invention are stable compounds and possess very good herbicidal properties against annual grasses of the genera Echinochloa, Setaria, Digitaria, Rottboellia, etc., grasses such as Lolium species and against many dicotyledonous weeds such as Amaranthus, Sesbania, Chrysanthemum, without causing damage to the cultivated plants in respect of which the use of the active substances is intended, for example, soya, alfalfa, peas, cotton, maize, sugar beet, sugar cane, Brassica species such as rape and cabbage, also cereals, such as barley and wheat.

As selective herbicides the active substances are applied before the germination of the cultivated plants and of the weeds and grasses. The rates of application are between 0.1 and 10 kg of active substance per hectare. But in pre-emergent application the weeds are virtually destroyed with a rate of application as low as 0.25 kg of active substance per hectare. Normally up to 10 kg of active substance per hectare are used for retarding the growth of established plants. Railway embankments, factory grounds, roads etc. may thus be prevented from becoming overgrown with weeds.

The new active substances of the formula I delay the growth in height of grass in grasslands and increase the tillering.

EXAMPLE 2

Combating of undesirable grasses in various cultures of useful plants (preemergence method)

One day after the test plants have been sown in seed dishes, dilute aqueous suspensions of the active substances are sprayed in such concentrations on the surface of the soil as to correspond to rates of application of 2 kg, 1 kg and 0.5 kg per hectare. The seed dishes are kept at 22° and 25° C. and about 70% relative humidity. The test is evaluated after 28 days according to the following linear rating:

```
         9 = plants undamaged (as control test)
         1 = plants destroyed
       8-2 = intermediate stages of damage
         — = not tested
             Weeds tested:
Echinochloa crus galli   = barnyard grass
Setaria italica          = Italian foxtail
Digitaria                = crab grass
Rottboellia              = raoul grass
Cyperus esculentus       = Yellow nutsedge
Alopecurus myosuroides   = black grass
Lolium perenne           = perennial rye grass
Avena fatua              = wild oat
```

According to the statement, following Table VII of Example 85 in U.S. Pat. No. 3,547,620 the closest comparable compounds are those of the formula

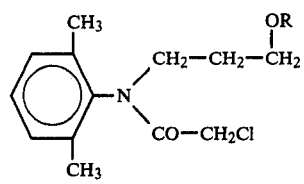

with R being either methyl (comp. A) or ethyl (comp. B). These compounds were tested in order to demonstrate the unpredictable improvement in the overall herbicidal performance of compounds of the formula I in which the alkoxy group is attached at the β- rather than the γ-position of the propyl group.

The results are given in the following Table.

EXAMPLE 3

The results of the following test prove the compounds of the invention to be stable on pre-emergent application for a period of time sufficient to keep a culture weed-free almost until the end of the season.

Arable soil comprising ca. 4% (b.w.) organic substance, 21% clay, 32% silt and 43% sand and contained in a plastic basin (50 cm×32 cm×7 cm) was sprayed with test substance in the form of a broth prepared from an emulsion concentrate to give an active substance concentration equivalent to 2 kg/hectare. Two parallel rows of weeds were sown in each basin and a further two rows were sown weekly over the next 7 weeks. Setaria italica was choosen as test weed since it is especially sensitive to compounds of type under test.

The condition of the weeds in each set of two rows was evaluated 3 weeds after sowing. The test conditions were: temp. 19°–23° C.; rel. humidity 50–60%; watering—normal.

Key as in example 2.

| Compd. | Weeks | | | | | | |
|--------|---|---|---|---|---|---|---|
|        | 0 | 1 | 2 | 3 | 4 | 5 | 6 |
| No. 1  | 2 | 1 | 2 | 2 | 2 | 3 | 4 |
| No. 2  | 1 | 1 | 1 | 2 | 2 | 4 | 4 |

The agents according to the invention are manufactured in known manner by intimately mixing and/or grinding active substances of the formula I with the suitable carriers, optionally with the addition of dispersants or solvents which are inert towards the active substances.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomacous earth, precipitated silica, alkaline

TABLE

| Rate of application | Compound | Echin-ochloa | Setaria | Dig-itaria | Rott-boellia | Cyperus | Alo-pecurus | Lolium | Avena fatua | Alfalfa | Sugar beet | Cotton | Soya | Barley |
|---|---|---|---|---|---|---|---|---|---|---|---|---|---|---|
| 2 kg | No. 1 | 1 | 1 | 1 | 2 | 1 | 1 | 1 | 2 | 7 | 8 | 9 | 9 | 6 |
| 1 kg |  | 1 | 1 | 1 | 5 | 1 | 1 | 1 | 5 | 7 | 9 | 9 | 9 | 9 |
| 0.5 kg |  | 1 | 1 | 1 | 6 | 1 | 5 | 1 | 6 | 8 | 9 | 9 | 9 | 9 |
| 2 kg | No. 2 | 1 | 1 | 1 | 1 | 1 | 1 | 1 | 2 | 6 | 7 | 8 | 8 | 6 |
| 1 kg |  | 1 | 1 | 1 | 3 | 1 | 2 | 2 | 4 | 6 | 8 | 9 | 8 | 6 |
| 0.5 kg |  | 1 | 1 | 1 | 5 | 1 | 3 | 3 | 5 | 8 | 9 | 9 | 9 | 9 |
| 2 kg | A | 1 | 3 | 1 | 4 | — | 5 | 3 | 7 | 9 | 9 | 9 | 9 | 6 |
| 1 kg |  | 1 | 5 | 2 | 7 | 1 | 6 | 6 | 9 | 9 | 9 | 9 | 9 | 7 |
| 0.5 kg |  | 2 | 8 | 7 | 9 | — | 8 | 9 | 9 | 9 | 9 | 9 | 9 | 9 |
| 2 kg |  | 1 | 2 | 1 | 6 | — | 8 | 3 | 4 | 7 | 9 | 9 | 9 | 8 |
| 1 kg | B | 4 | 6 | 3 | 7 | 1 | 8 | 5 | 9 | 9 | 9 | 9 | 9 | 9 |
| 0.5 kg |  | 6 | 9 | 9 | 9 | — | 9 | 9 | 9 | 9 | 9 | 9 | 9 | 9 |
|  |  | undesirable grasses | | | | | | | | useful plants | | | | |

At the high application rate of 2 kg a.i./hectare comparative compounds A and B possess insufficient activity and are useless for practical purposes.

Compounds Nos. 1 and 2 of the invention display a broad spectrum of weedicidal activity and can be used in all the cultures given in the Table, depending on the application rate. Thus, it is proved that they fulfil two of the three desiderata for a selective herbicide, to wit activity and selectivity. The third requirement of long lasting activity in the soil is proved in the following Example 3.

earth silicates, sodium and potassium aluminium silicates (feldspar and mica), calcium and magnesium sulphates, fertilisers, for example ammonium sulphate, ammonium phosphate, ammonium nitrate, urea, ground vegetable products, such as corn meal, bark dust, sawdust, nutshell meal, etc.

The particle size of the carriers for dusts is advantageously up to 0.1 mm, for tracking agents from about 0.075 to 0.2 mm, and for granules 0.2 mm or larger.

The solid forms contain the active substances in concentrations from 0.5 to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substance with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid and salts of sulphated fatty alcohol glycol ethers.

Suitable anti-foam agents are silicones.

The active substance is so mixed, ground sieved and strained with the additives mentioned above that, in wettable powders, the solid particle size of from 0.02 to 0.04 mm, and in pastes, of 0.03 mm is not exceeded.

The agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substance of the formula I. The agents according to the invention may also contain plant fertilisers, trace elements etc.

The active substances of the formula I can, for example, be formulated as follows. The parts denote parts by weight.

Granules

The following substances are used to manufacture 5% granules:
5 parts of active substance
0.25 parts of epichlorohydrin,
0.25 parts of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable powder

The following constituents are used to manufacture (a) a 70%, (b) a 25% and (c) a 10% wettable powder:

(a)

70 parts of active substance
5 parts of sodium dibutylnaphthalene sulphonate,
3 parts of naphthalenesulphonic acid/phenolsulphonic acid/formaldehyde condensate (3:2:1),
20 parts of kaolin,
22 parts of Champagne chalk;

(b)

25 parts of active substance
5 parts of oleylmethyltaurid-sodium-salt,
2.5 parts of naphthalenesulphonic acid/formaldehyde condensate,
0.5 part of carboxymethyl cellulose,
5 parts of neutral potassium-aluminium-silicate,
62 parts of kaolin;

(c)

10 parts of active substance
3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with the 10-fold amount of water it is possible to obtain suspensions containing 7%, 2.5% and 1% of active substance.

Paste

The following substances are used to manufacture a 45% paste:
45 parts of active substance
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of any desired concentration.

Emulsion Concentrate

To manufacture a 25% emulsion concentrate
25 parts of active substance
5 parts of a mixture of nonylphenolpolyoxy-ethoxyethylene and calcium dodecylenesulphonate,
35 parts of 3,5,5-trimethyl-2-cyclohexan-1-one,
35 parts of dimethyl formamide, are mixed together. This concentrate can be diluted with water to give emulsions in desired concentrations. Such emulsions are suitable for combating weeds in cultures of crop plants.

What we claim is:
1. A compound of the formula I

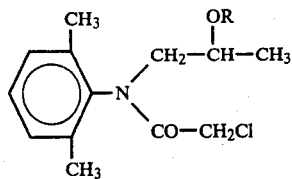 (I)

wherein R represents methyl or ethyl.

2. A composition for combating weeds and retarding plant growth which comprises as active ingredient an effective amount of a compound according to claim 1, together with a suitable carrier.

3. A method of selectively combating undesirable plant growth in cultures of useful crops, which comprises applying to the crop area before emergence of the plants a compound as claimed in claim 1.

4. A method of retarding plant growth, which comprises applying to emerged plants a compound according to claim 1.

* * * * *